United States Patent [19]

Guay et al.

[11] Patent Number: 5,710,160
[45] Date of Patent: Jan. 20, 1998

[54] DIPHENYL PYRIDYL ETHANE DERIVATIVES AS PDE IV INHIBITORS

[75] Inventors: Daniel Guay, Ille Perrot; Yves Girard, Ille Bizard; Yves Ducharme, Montreal, all of Canada

[73] Assignee: Merck Frosst Canada, Inc., Kirkland, Canada

[21] Appl. No.: 763,565

[22] Filed: Dec. 10, 1996

[51] Int. Cl.$^6$ ............... A61K 31/44; A61K 31/40; C07D 213/53; C07D 235/04
[52] U.S. Cl. ............... 514/277; 514/256; 514/255; 514/340; 514/357; 514/396; 546/266; 546/272.7; 548/203
[58] Field of Search ............... 546/266, 272.7; 548/203; 514/277, 256, 255, 340, 357, 396

[56] References Cited

U.S. PATENT DOCUMENTS 4,882,343  11/1989  Cordi ............... 514/341
5,580,888  12/1996  Warrellow ............... 514/332

FOREIGN PATENT DOCUMENTS

WO 94/14742  7/1994  WIPO.
WO 94/20446  9/1994  WIPO.
WO 95/17386  6/1995  WIPO.

OTHER PUBLICATIONS

The Merck Index; S. Budavari (Ed.); 12th Edition: "An encyclopedia of chemicals, drugs, and biologicals" 1996, Merck Research Laboratories, Whitehouse Station, N.J. ISBN 0911910-12-3 XP002027526, See monograph 8410.
Chemical Abstracts #125:132083 by Gozzard, 1996.
Chemical Abstracts #125:158239 by Holbrook, 1996.
Chemical Abstracts #125:185440, 1996.
Chemical Abstracts #124:260848, 1995.
Chemical Abstracts #124:260846, 1995.
Chemical Abstracts #123:286011, 1995.
Chemical Abstracts #122:265044, 1994.

*Primary Examiner*—Alan L. Rotman
*Assistant Examiner*—D. Margaret M. Mach
*Attorney, Agent, or Firm*—Curtis C. Panzer; David L. Rose

[57] ABSTRACT

The invention encompasses the novel compound of Formula I useful in the treatment of diseases, including asthma, by raising the level of cyclic adenosine-3',5'-monophosphate (cAMP) through the inhibition of phosphodiesterase IV (PDE IV).

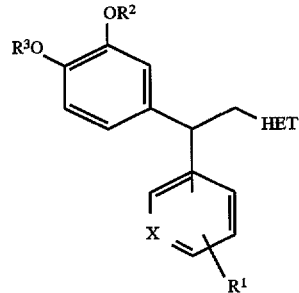

The invention also encompasses certain pharmaceutical compositions and methods for treatment of diseases by inhibition of PDE IV, resulting in an elevation of cAMP, comprising the use of compounds of Formula I.

9 Claims, No Drawings

DIPHENYL PYRIDYL ETHANE DERIVATIVES AS PDE IV INHIBITORS

BACKGROUND OF THE INVENTION

This invention relates to compounds and pharmaceutical compositions for the treatment of diseases by raising the level of cyclic adenosine-3',5'-monophosphate (cAMP) through the inhibition of phosphodiesterase IV (PDE IV).

Many hormones and neurotransmitters modulate tissue function by elevating intra-cellular levels of adenosine 3',5'-cyclic monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I–VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155 and Nicholson et al (1991) TIPS, 12: 19–27].

The availability of PDE isotype selective inhibitors has enabled the role of PDEs in a variety of cell types to be investigated. In particular it has been established that PDE IV controls the breakdown of cAMP in many inflammatory cells, for example, basophils (Peachell P. T. et al., (1992) *J. Immunol.* 148 2503–2510) and eosinophils (Dent G. et al., (1991) *Br. J. Pharmacol.* 103 1339–1346) and that inhibition of this isotype is associated with the inhibition of cell activation. Furthermore, elevation of cAMP in airway smooth muscle has a spasmolytic effect. Consequently PDE IV inhibitors are currently being developed as potential anti-inflammatory drugs particularly for the prophylaxis and treatment of asthma, by achieving both anti-inflammatory and bronchodilator effects.

The application of molecular cloning to the study of PDEs has revealed that for each isotype there may be one or more isoforms. For PDE IV, it is has been shown that there are four isoforms (A, B, C and D) each coded for by a separate gene in both rodents (Swinnen J. V. et al., (1989) *Proc. Natl. Acad. Sci. USA* 86 5325–5329) and man (Bolger G. et al., (1993) *Mol. Cell Biol.* 13 6558–6571).

The existence of multiple PDE IVs raises the prospect of obtaining inhibitors that are selective for individual isoforms, thus increasing the specificity of action of such inhibitors. This assumes that the different PDE IV isoforms are functionally distinct. Indirect evidence in support of this comes from the selective distribution of these isoforms in different tissues (Swinnen et al., 1989; Bolger et al., 1993; Obernolte R. et al., (1993) *Gene* 129 239–247, ibid) and the high degree of sequence conservation amongst isoforms of different species.

To date full length cDNAs for human PDE IVA, B and D (Bolger et al., 1993 ibid; Obernolte et al., 1993 ibid; Mclaughlin M. et al., (1993) *J. Biol. Chem.* 268 6470–6476) and rat PDE IVA, B and D (Davis R. et al., (1989) *Proc. Natl. Acad. Sci. USA* 86 3604–3608; Swinnen J. V. et al., (1991) *J. Biol. Chem.* 266 18370–18377), have been reported, enabling functional recombinant enzymes to be produced by expression of the cDNAs in an appropriate host cell. These cDNAs have been isolated by conventional hybridisation methods. However using this approach, only partial cDNAs for both human and rat PDE IVC have been obtained. (Bolger et al., ibid. 1993 and Swinnen et al., ibid. 1989 and International Patent Specification No. WO 91/16457.)

The design of PDE IV inhibitors for the treatment of inflammatory diseases such as asthma, has met with limited success to date. Many of the PDE IV inhibitors which have been synthesised have lacked potency and/or inhibit more than one type of PDE isoenzyme in a non-selective manner. PDE IV inhibitors that are relatively potent and selective for PDE IV, are reported to be emetic as well. Indeed this side effect has been so universal that experts have expressed their belief that the emesis experienced upon administration of a PDE IV inhibitor, may be mechanism based.

We have now found a novel series of tri-substituted phenyl derivatives, members of which compared to known structurally similar compounds are potent inhibitors of PDE IV at concentrations at which they have little or no inhibitory action on other PDE isoenzymes. These compounds inhibit the human recombinant PDE IV enzyme and also elevate cAMP in isolated leukocytes. Certain compounds prevent inflammation in the lungs induced by carrageenan, platelet-activating factor (PAF), interleukin-5 (IL-5) or antigen challenge. These compounds also suppress the hyperresponsiveness of airway smooth muscle seen in inflamed lungs. Advantageously, compounds according to the invention have good oral activity and at orally effective doses exhibit little or none of the side-effects associated with known PDE IV inhibitors, such as rolipram. The compounds of the invention are therefore of use in medicine, especially in the prophylaxis and treatment of asthma and other inflammatory conditions.

SUMMARY OF THE INVENTION

The invention encompasses novel compounds of Formula I useful in the treatment of disease by inhibition of PDE IV, resulting in an elevation of cAMP.

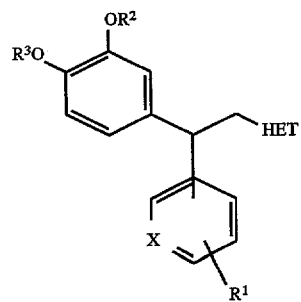

The invention also encompasses certain pharmaceutical compositions and methods for treatment of diseases by inhibition of PDE IV, resulting in an elevation of cAMP, comprising the use of compounds of Formula I.

DETAILED DESCRIPTION OF THE INVENTION

The invention encompasses the novel compound of Formula I useful in the treatment of disease by inhibition of PDE IV, resulting in an elevation of cAMP,

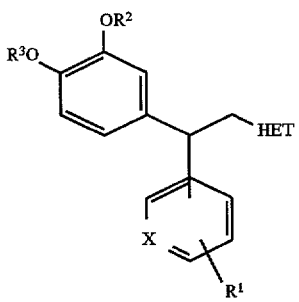

or a pharmaceutically acceptable salt thereof wherein:
$R^1$ is selected from
(a) —CH=NOH,
(b) —CH(OH)—CH$_3$,
(c) —CO—CH$_3$,
(d) —CO—N[CH$_2$CH$_2$]$_2$N—CH$_3$;
(e) —CO—N[CH$_2$CH$_2$CH$_2$CH$_2$], and
(f) —5—tetrazolyl;

$R^2$ and $R^3$ are independently selected from
(a) C$_{1-7}$alkyl,
(b) substituted C1-7 alkyl, wherein the substituent is F, Cl, Br or I,
(c) 2-phenethyl or 2-indanyl, optionally mono or di-substituted on the benzene ring, wherein the substituents are independently selected from the group consisting of
(1) halo,
(2) C$_{1-6}$alkoxy,
(3) C$_{1-6}$alkylthio,
(4) CN,
(5) CF$_3$,
(6) C$_{1-6}$alkyl,
(7) N$_3$,
(8) —CO$_2$H, $R^4$ is selected from
(a) hydrogen,
(b) C$_{1-6}$alkyl,
(c) phenyl, benzyl or 2-phenethyl, optionally mono or di-substituted on the benzene ring, wherein the substituents are independently selected from the group consisting of
(1) halo,
(2) C$_{1-6}$alkoxy,
(3) C$_{1-6}$alkylthio,
(4) CN,
(5) CF$_3$,
(6) C$_{1-6}$alkyl,
(7) N$_3$,
(8) —CO$_2$H, $R_5$ and $R_8$ are each independently selected from
(a) —CF$_3$,
(b) C$_{1-6}$alkyl,
(c) phenyl, benzyl or 2-phenethyl, optionally mono or di-substituted on the benzene ring, wherein the substituents are independently selected from the group consisting of
(1) halo,
(2) C$_{1-6}$alkoxy,
(3) C$_{1-6}$alkylthio,
(4) CN,
(5) CF$_3$,
(6) C$_{1-6}$alkyl,
(7) N$_3$,
(8) —CO$_2$H, $R^6$ and $R^7$ are independently selected from
(a) hydrogen, and
(b) C$_{1-6}$alkyl, or
$R^6$ and $R^7$ may be joined to form a saturated 5, 6 or 7 membered heterocycle, said heterocycle containing a heteroatom which is nitrogen and optionally containing an additional hetero atom which is O or S atom or NR$^4$, and optionally containing a carbonyl group;

HET is selected from pyridyl or imidazolyl, optionally mono or di-substituted with substitutents selected from the group consisting of halo, C$_{1-6}$alkyl, C$_{1-6}$alkoxy, C$_{1-6}$alkylthio, benzyl, 2-phenethyl, NHCOR$^5$, NR$^6$R$^7$, NHS(O)$_2$R$^8$, OH, CN, or CF$_3$, and the N-oxides thereof;
X is selected from N, N→O or CH.

Within this embodiment, there is a genus of compounds wherein
$R^2$ is cyclopentyl, optionally mono or di or tri-substituted with substituents selected from the group consisting of F, Cl, Br and I, and
$R^3$ is methyl.

Within this genus there is a class of compounds wherein
$R^1$ is selected from
(a) —CH=NOH,
(b) —CH(OH)—CH$_3$,
(c) —CO—CH$_3$,
(d) —CO—N[CH$_2$CH$_2$]$_2$N—CH$_3$;
(e) —CO—N[CH$_2$CH$_2$CH$_2$CH$_2$], and
(f) —5—tetrazolyl;
$R^2$ is cyclopentyl,
$R^3$ is methyl,
$R^5$ and $R^8$ are each independently selected from
(a) —CF$_3$,
(b) C$_{1-3}$alkyl,
(c) phenyl, benzyl or 2-phenethyl, optionally mono or di-substituted on the benzene ring, wherein the substituents are independently selected from the group consisting of
(1) halo,
(2) C$_{1-3}$alkoxy,
(3) C$_{1-3}$alkylthio,
(4) CN,
(5) CF$_3$,
(6) C$_{1-3}$alkyl,
(7) N$_3$,
(8) —CO$_2$H, $R^6$ and $R^7$ are independently selected from
(a) hydrogen, and
(b) C$_{1-3}$alkyl, or
$R^6$ and $R^7$ may be joined to form a saturated 5, 6 or 7 membered heterocycle, said heterocycle containing a heteroatom which is nitrogen and optionally containing an additional hetero atom which is O or S atom or NR$^4$, and optionally containing a carbonyl group;
HET is selected from
pyridyl or imidazolyl, optionally mono or di-substituted with substitutents selected from the group consisting of halo, C$_{1-6}$alkyl, C$_{1-6}$alkoxy, C$_{1-6}$alkylthio, benzyl, 2-phenethyl, NHCOR$^5$, NR$^6$R$^7$, NHS(O)$_2$R$^8$, OH, CN, or CF$_3$, and the N-oxides thereof;
X is selected from N, N→O or CH.

Within this class there is a sub-class of compounds wherein $R^1$ is selected from
(a) —CH=NOH,
(b) —CH(OH)—CH$_3$,
(c) —CO—CH$_3$,
(d) —CO—N[CH$_2$CH$_2$]$_2$N—CH$_3$;
(e) —CO—N[CH$_2$CH$_2$CH$_2$CH$_2$], and
(f) —5—tetrazolyl;
$R^2$ is cyclopentyl,
$R^3$ is methyl,
$R^5$ and $R^8$ are each independently selected from
(a) —CF$_3$,
(b) C$_{1-3}$alkyl,
$R^6$ and $R^7$ are independently selected from (a) hydrogen, and
(b) $C_{1-3}$alkyl, or $R^6$ and $R^7$ may be joined to form a saturated 5, 6 or 7 membered heterocycle, said heterocycle containing a heteroatom which is nitrogen and optionally containing an additional hetero atom which is O or S atom or $NR^4$, and optionally containing a carbonyl group;

HET is selected from pyridyl, optionally mono or di-substituted with substitutents selected from the group consisting of halo, $C_{1-6}$alkyl, $C_{1-6}$alkoxy, $C_{1-6}$alkylthio, benzyl, 2-phenethyl, $NHCOR^5$, $NR^6R^7$, $NHS(O)_2R^8$, OH, CN, or $CF_3$, and the N-oxides thereof;

X is selected from CH.

As will be appreciated by those of skill in the art, Halo is intended to include F, Cl, Br and I.

For purposes of this specification alkyl is defined to include linear, branched, and cyclic structures, with $C_{1-6}$alkyl including including methyl, ethyl, propyl, 2-propyl, s- and t-butyl, butyl, pentyl, hexyl, 1,1-dimethylethyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of alkoxy groups include methoxy, ethoxy, propoxy, isopropoxy, cyclopropyloxy, cyclohexyloxy, and the like. Likewise, $C_{1-6}$alkylthio is intended to include alkylthio groups of from 1 to 6 carbon atoms of a straight, branched or cyclic configuration. Examples of alkylthio groups include methylthio, propylthio, isopropylthio, cycloheptylthio, etc. By way of illustration, the propylthio group signifies $-SCH_2CH_2CH_3$. $C_{1-6}$haloalkyl means an alkyl group in which two or more hydrogen atoms have been replaced by halogen atoms.

Exemplifying the invention are:

(a) (R)-4-{2-(3-Cyclopentyloxy-4-methoxyphenyl)-2-[4-(4-methylpiperazinocarbonyl)phenyl]ethyl}pyridine, (b) (R)-4-[2-(3-Cyclopentyloxy-4-methoxyphenyl)-2-(4-pyrrolidinocarbonylphenyl)ethyl]pyridine, (c) (R)-4-[1-(3-Cyclopentyloxy-4-methoxyphenyl)-2-(4-pyridyl) ethyl]benzaldehyde oxime, (d) (R)-4-{2-(3-Cyclopentyloxy-4-methoxyphenyl)-2-[4-(tetrazol-5-yl)phenyl]ethyl}pyridine, (e) (R)-4-{2-(3-Cyclopentyloxy-4-methoxyphenyl)-2-[4-(1-hydroxyethyl) phenyl]ethyl}pyridine, and (f) (R)-4-[2-(3-Cyclopentyloxy-4-methoxyphenyl)-2-(4-acetylphenyl) ethyl]pyridine.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

In a second embodiment, the invention encompasses pharmaceutical compositions for treatment of disease by inhibition of PDE IV, as disclosed herein comprising a pharmaceutically acceptable carrier and a non-toxic therapeutically effective amount of compound of formula I as described above.

Within this embodiment the invention encompasses pharmaceutical compositions for treatment of disease by inhibition of PDE IV, resulting in an elevation of cAMP, as disclosed herein comprising a pharmaceutically acceptable carrier and a non-toxic therapeutically effective amount of compound of formula I as described above.

For purposes of this specification a compound is said to selectively inhibit PDE IV in preference to other PDE's if the ratio of the IC50 concentration for all other PDE inhibition to PDE IV inhibition is 100 or greater.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts. Compounds according to the invention are selective and potent inhibitors of PDE IV. The ability of the compounds to act in this way may be simply determined by the tests described in the Examples hereinafter.

The compounds according to the invention are thus of particular use in the prophylaxis and treatment of human diseases where an unwanted inflammatory response or muscular spasm (for example bladder or alimentary smooth muscle spasm) is present and where the elevation of cAMP levels may be expected to prevent or alleviate the inflammation and relax muscle.

Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and artherosclerosis.

Compounds of the invention also suppress neurogenic inflammation through elevation of cAMP in sensory neurones. They are, therefore, analgesic, anti-tussive and anti-hyperalgesic in inflammatory diseases associated with irritation and pain. Compounds according to the invention may also elevate cAMP in lymphocytes and thereby suppress unwanted lymphocyte activation in immune-based diseases such as rheumatoid arthritis, ankylosing spondylitis, transplant rejection and graft versus host disease.

Compounds according to the invention have also been found to reduce gastric acid secretion and therefore can be used to treat conditions associated with hypersecretion of gastric acid.

Compounds of the invention suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention suppress inflammation and pyrexia due to cytokines and are, therefore, useful in the treatment of inflammation and cytokine-mediated chronic tissue degeneration which occurs in diseases such as rheumatoid or osteo-arthritis.

Over-production of cytokines such as TNF in bacterial, fungal or viral infections or in diseases such as cancer, leads to cachexia and muscle wasting. Compounds of the invention ameliorate these symptoms with a consequent enhancement of quality of life.

Compounds of the invention also elevate cAMP in certain areas of the brain and thereby counteract depression and memory impairment.

Compounds of the invention suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

For the treatment of any of these, compounds of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. No. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethyleneoxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Methods of Synthesis

The compounds of the present invention can be prepared according to WO 94/14742, published on 7 Jul. 1994, or according to WO 95/17386, published on 29 Jun. 1995, which are hereby incorporated by reference or by the methods described below. It will be apparent to one skilled in the art that similar methodology could be used to prepare the enantiomers or the racemates of the illustrated compounds.

CHEMISTRY

Scheme 1

Carboxylic acid derivatives were prepared by the method presented in Scheme 1. The diastereoselective addition of Grignard reagents derived from suitable bromoaryl-1,3-dioxolanes to acylsultam Michael acceptor II afforded triarylpropanoylsultam intermediates. Removal of the chiral auxiliary, subsequent decarboxylation and aldehyde deprotection were then performed in a one-pot fashion by successive treatment with a suitable lithium thiolate followed by a saponification with aqueous hydroxide and then by an aqueous acidic treatment. In this way, arenecarboxaldehyde intermediates 1 were obtained. Oxidation of those by sodium chlorite gave access to arenecarboxylic acid intermediates 2. Carboxylic amides were prepared by treating acids 2 with amines in the presence of diethyl cyanophosphonate and triethylamine.

Scheme 2

Reaction of hydroxylamine hydrochloride with arenecarboxaldehyde intermediates 1 gave access to oxime derivatives (Scheme 2). Dehydration of these oximes with trichloromethyl chloroformate (or other suitable dehydrating agent such as acetic anhydride, ethyl orthgoformate/H$^+$, CCl$_3$COCl/Et$_3$N, etc.) yielded the corresponding arenenitriles which were transformed into 5-tetrazolyl derivatives following reaction with a suitable azide.

Scheme 3

Addition of methylmagnesium bromide to arenecarboxaldehyde intermediates 1 gave the corresponding secondary alcohols which were oxidized with pyridinium chlorochromate to afford the acetyl derivatives.

Scheme 1

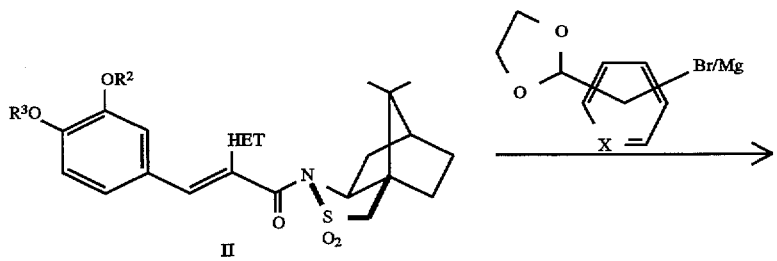

-continued
Scheme 1
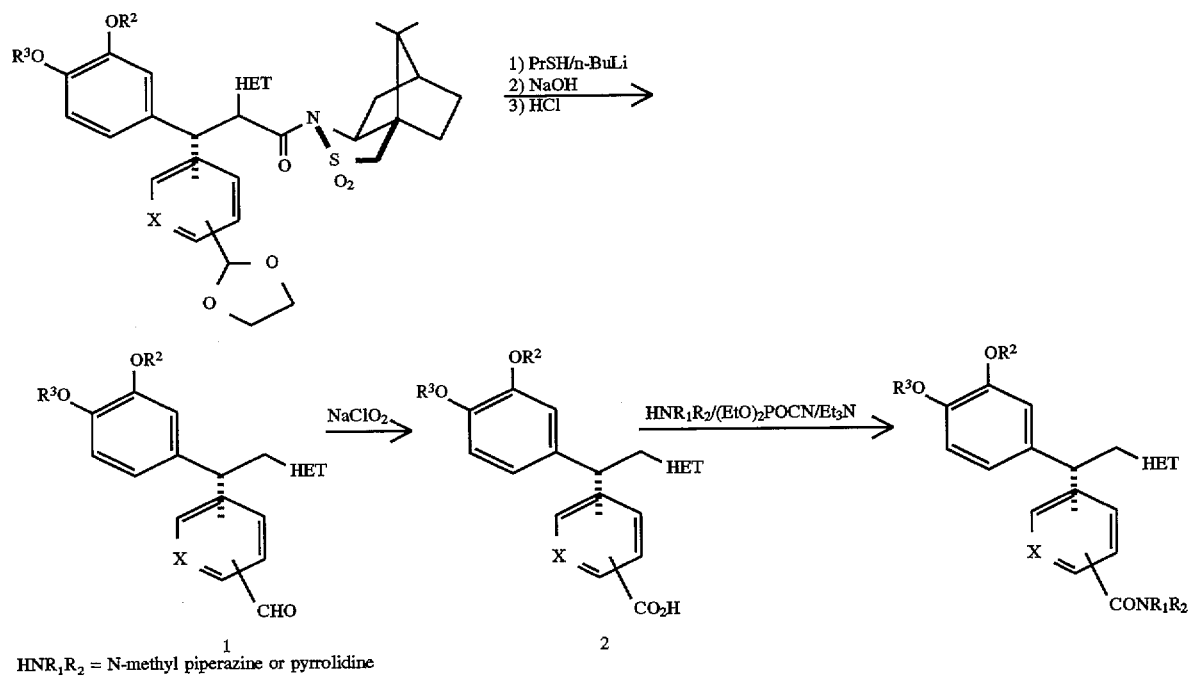
HNR₁R₂ = N-methyl piperazine or pyrrolidine
-continued
Scheme 2
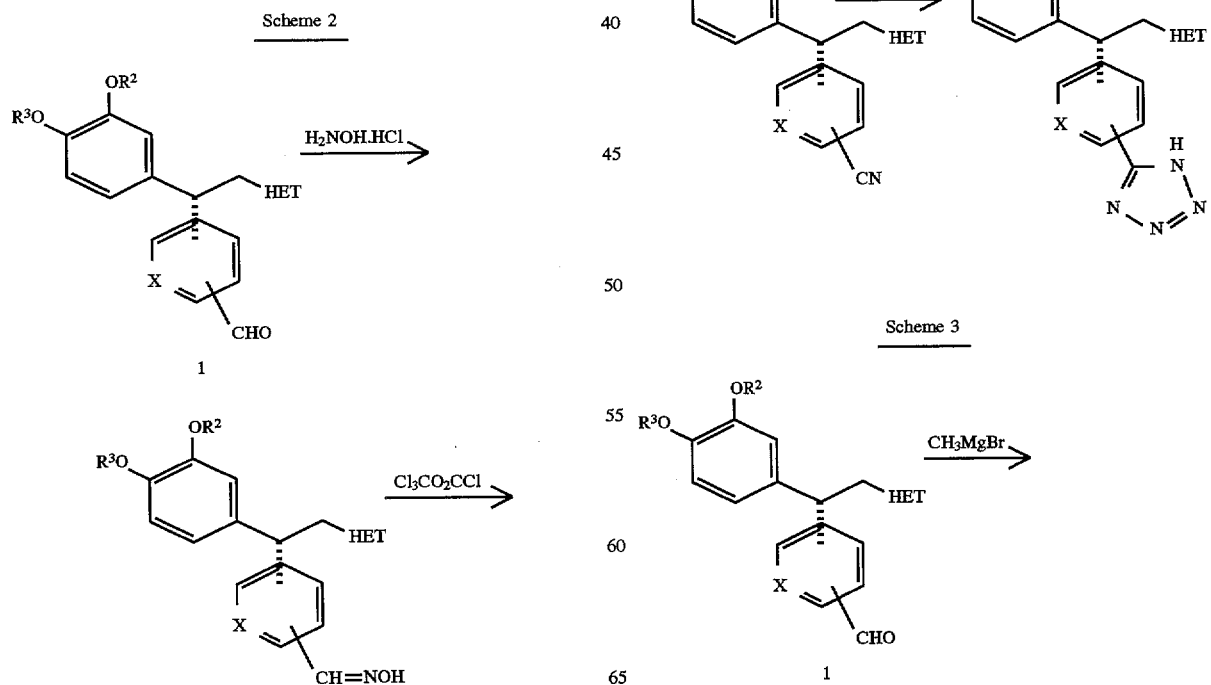
Scheme 3

13

-continued

Scheme 3

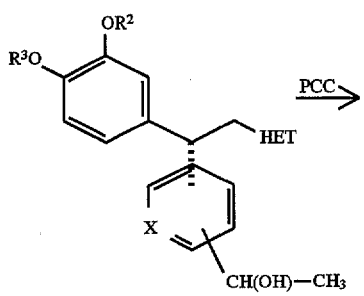

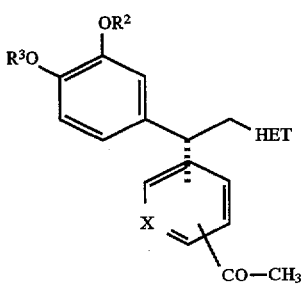

Representative compounds

Table 1 illustrates the compounds of the instant invention:

TABLE 1

| EX. | R¹ | Scheme |
|---|---|---|
| 1 | CO—N⟨  ⟩N—CH₃ | |
| 2 | CO—N⟨  ⟩ | |
| 3 | CH=NOH | |
| 4 | 5-tetrazolyl | |
| 5 | CH(OH)—CH₃ | |
| 6 | CO—CH₃ | |

14

TABLE 2

In Vitro Potency of PDE IV inhibitors.

| EX. | $IC_{50}$ (nM) GST-Met 248 PDE IVa |
|---|---|
| 1 | 0.8 |
| 2 | 1 |
| 3 | 3 |
| 4 | 2 |
| 5 | 2 |
| 6 | 3 |

Assays for Determining Biological Activity

Establishment of CHO-K1 cell lines stably expressing PDE IVa enzyme

CHO-K1 cells stably expressing the prostacyclin receptor and grown under G418 selection as described previously (Y. Boie, et al, J. Biol. Chem.: 269, 12173–12178, 1994) were plated at a density of $1.75 \times 10^6$ cells/175 cm² in a T-175 flask (Gibco, Burlington, Vt.) containing alpha MEM media; 10% heat inactivated fetal bovine serum (FBS); 1% (v/v) penicillin/streptomycin; 25 mM Hepes, pH 7.4; and 500 mg/ml G418 (complete media). The cells were placed in an incubator for 24 hr at 37° C. and 5% $CO_2$. The cells were then washed with warmed sterile phosphate buffered saline (PBS) and incubated with 2 mg/ml DNA, and 9 mg/ml lipofectamine reagent in Opti-MEM for 7 hr. At 37° C. and 5% $CO_2$. The incubation solution was diluted 1:2 with Opti-MEM containing 20% FBS and incubated overnight. Following the overnight incubation, the media was replaced by complete media containing 500 mg/ml hygromycin B. Colonies were identified and gown in T-175 flasks for further characterization.

Measurement of whole-cell cAMP content

CHO-K1 cells were plated at a density of $10^6$ cells/175 cm² containing complete media with 500 mg/ml hygromycin. The flasks were maintained in an incubator at 37° C. with 5.0% $CO_2$ for 72 hr. The media was changed and the cells were allowed to grow overnight. The cells were washed and dissociated from the plate with PBS containing 0.5 mM EDTA. Cellular cAMP content was measured by centrifuging the cell suspension at 150 g×10 min. And resuspending the cells in a Hanks buffered salt solution at a density of $0.2 \times 10^6$ cells/ml. The cells were preincubated at room temperature for 15 min. and then incubated with 10 mM prostaglandin $I_2$ ($PGI_2$) and the indicated compound for an additional 10 min. Basal cAMP levels were determined by incubating the cells in 0.1% DMSO. The incubations were terminated by the addition of HCl (0.1N final) and the cells measured for cAMP as described below.

Determinations of whole-cell cAMP content were performed by incubating 100 ml reconstituted rabbit anti-succinyl cAMP serum with 100 ml of the whole-cell reaction or known cAMP standard and 30 pmol of [125]I-cAMP TME in a ScintiStrip™ well (300 ml final volume) at room temperature for 18 h. Total cpm ($B_o$) was determined in the absence of sample of cAMP standard. The reaction mixture was then aspirated out of the well, and the individual wells were counted in a Beckman LS 6000SC with the window open from 10–999 for 1 min. The data were expressed as $\%B/B_o = [(\text{standard or sample cpm} - \text{non-specific cpm})/(B_o \text{ cpm} - \text{non-specific cpm})] \times 100$. Non-specific cpm were determined by incubating only the [125]I-cAMP TME with assay buffer (50 nM acetate; pH 5.8) in the ScintiStrip™ well. All determinations were performed in triplicate.

Phosphodiesterase Scintillation Proximity Assay

CHO-K1 cells were lysed by sonication for 10 secs at a power setting of 50% (Braunsonic Model 2000) in an ice cold solution containing 50 mM Tris, pH 7.5; 1 mM EDTA; and 200 mM b-mercaptoethanol.

The soluble and particulate fractions of the cell were obtained by centrifuging the sonicate for 90 min. at 100,000 x g at 4° C. PDE activity was measured in a solution containing 50 mM Tris, pH 7.5; 10 mM $MgCl_2$; 1 mM EDTA; and 100 nM (or indicated) $^3$H-cAMP (100 ml final volume) in the presence of varying concentrations of inhibitor. The reaction mixture containing enzyme was incubated for 10 min. at 30° C. in 96-well View Plates (Packard), and terminated by the addition of 50 ml Phosphodiesterase Scintillation Proximity Assay (SPA) Beads (Amersham) containing 18 mM $ZnSO_4$. The amount of $^3$H-cAMP hydrolysis was determined by counting the plates in a Wallac 1450 mBeta LSC counter.

The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intra-peritoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 main prior to measurement of cAMP by specific radioimmunoassay (DuPont).

The most potent compounds according to the Examples induced a concentration -dependent elevation of cAMP in neutrophils and/or eosinophils at concentrations of 0.1 nM to 1 mM.

Suppression of Leukocyte Function

Compounds of the invention were investigated for theft effects on superoxide generation, chemotaxis and adhesion of neutrophils and eosinophils. Isolated leukocytes were incubated with dihydrocytochalsin B for superoxide generation only and test compound prior to stimulation with FMLP. The most potent compounds of the Examples caused a concentration-dependent inhibition of superoxide generation, chemotaxis and adhesion at concentrations of 0.1 nM to 1 mM.

Lipopolysaccharide (LPS)-induced synthesis of tumour necrosis factor (TNF) by human peripheral blood monocytes (PBM) is inhibited by compounds of the Examples at concentrations of 0.01 nM to 10 mM.

Relaxation of Constricted Airway Smooth Muscle in vitro

The effects of compounds of the invention on guinea-pig isolated tracheal smooth muscle were investigated. Isolated tracheal rings were suspended in organ baths and immersed in oxygenated Krebs' solution. The smooth muscle was contracted with sub-maximal concentrations of histamine or carbachol prior to the addition of increasing concentrations of test compound to the organ baths. The most potent compounds of the Examples caused a concentration-dependent reversal of both histamine and carbachol-induced contractions at concentrations of 1 nM to 100 mM. The compounds were generally more potent in reversing histamine-induced tone than carbachol-induced tone.

Effects on Cardiac Muscle in vitro

Compounds of the invention have been tested for their effects on isolated cardiac muscle. Right atrial and papillary muscles were dissected out from the hearts of guinea pigs and suspended in organ baths for measuring the rate (chronotropic) of spontaneously beating atria and force (inotropic) of the electrically stimulated papillary muscle. In these preparations, selective PDE IV inhibitors such as rolipram do not have any direct effects whereas selective PDE III inhibitors such as milrinone have positive chronotropic and inotropic effects. The non-specific PDE inhibitor theophylline, which is used in asthma as a bronchodilator, also causes significant cardiovascular changes such as tachycardia. Selective PDE IV inhibitors have advantage over theophylline, therefore, through reduced cardiovascular side effects. The most potent and selective compounds of the Examples had no direct effects on the atrial and papillary muscles in vitro at concentrations up to 10 mM but in combination with PDE III inhibitors, these inhibitors showed an enhancement of chronotropic and inotropic activity, typical of selective type IV inhibitors.

Anti-inflammatory Activity in vivo

Inteleukin-5 (IL-5)-induced pleural eosinophilia in the rat (Lisle, et al, 1993, *Br.J. Pharmacol.* 108, 230p) is inhibited by compounds of the Examples given orally at doses of 0.0001 to 10.0 mg/kg. The most potent compounds cause a dose-dependent reduction in migrating eosinophils with $ED_{50}$s of 0.003 to 0.03 mg/kg p.o.

Compounds of the invention also reduce the inflammatory responses induced in rats by platelet activating factor (PAF).

Anti-allergic Activity in vivo

Compounds of the invention have been tested for effects on an IgE-mediated allergic pulmonary inflammation induced by inhalation of antigen by sensitised guinea pigs. Guinea pigs were initially sensitised to ovalbumin under mild cyclophosphamide-induced immunosuppression, by intraperitoneal injection of antigen in combinations with aluminium hydroxide and pertussis vaccine. Booster doses of antigen were given two and four weeks later and at six weeks, animals were challenged with aerosolised ovalbumin whilst under cover of an intraperitoneally administered anti-histamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the Examples.

Effects on Pulmonary Dynamics

Compounds of the invention (0.001–10 mg/kg by oral or other route of aministration) reduce the allergic bronchoconstruction caused by antigen in sensitized guinea pigs.

Compounds of the invention have been tested for their effects on ozone-induced hyperreactivity of the airways of guinea pigs. Following the inhalation of ozone, guinea pigs become very much more sensitive to the bronchoconstrictor effects of inhaled histamine than naive animals (Yeadon et al., 1992, *Pulmonary Pharm.,* 5, 39). There is a pronounced shift to the left (10–30 fold) of the dose response curve to histamine and a highly significant increase in the maximum increase in pulmonary resistance. Compounds of the Examples administered 1 h prior to ozone by the intraperitoneal or oral (0.001–10 mg/kg) route caused a dose-dependent inhibition of ozone-induced hyperreactivity.

Adverse Effects

Compounds of the invention are free from adverse effects following repeated overdosage to rats or dogs. For example, over administration of 125 mg/kg/day of active compounds of the Examples to rats for 30 days is not associated with adverse toxicity.

SPA based PDE activity assay protocol

Compounds which inhibit the hydrolysis of cAMP to AMP by the type-IV cAMP-specific phosphodiesterases were screened in 96-well plate format as follows:

In a 96 well-plate at 30° C. was added the test compound (dissolved in 2 ul DMSO), 188 ml of substrate buffer containing [2,8-$^3$H] adenosine 3',5'-cyclic phosphate (cAMP, 100 nM to 50 µM), 10 mM $MgCl_2$, 1 mM EDTA, 50 mM Tris, pH 7.5. The reaction was initiated by the addition of 10 ml of human recombinant PDE-IV (the amount was controlled so that ~10% product was formed in 10 min. at 30° C). The reaction was stopped after 10 min. by the addition of 1 mg of PDE-SPA beads (Amersham). The product AMP generated was quantified on a Microbeta 96-well plate counter. The signal in the absence of enzyme was defined as the background. 100% activity was defined as the signal detected in the presence of enzyme and DMSO with the background subtracted. Percentage of inhibition was calculated accordingly. $IC_{50}$ value was approximated with a non-linear regression fit of the standard 4-parameter/ multiple binding sites equation from a ten point titration.

$IC_{50}$ values shown in Table 2 were determined with 100 nM cAMP using the purified GST fusion protein of the human recombinant phosphodiesterase IVa (met-248) produced from a baculovirus/Sf-9 expression system.

The most potent compounds of the invention are 20–30 times less active than rolipram in inducing behavioural changes, sedation or emesis in rats, ferrets or dogs.

The invention will now be illustrated by the following non-limiting examples in which, unless stated otherwise:

(i) all operations were carried out at room or ambient temperature, that is, at a temperature in the range 18°–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The following abbreviations have the indicated meanings:
Ac=acetyl
Bn=benzyl
cAMP cyclic adenosine-3',5'-monophosphate
DBU=1,8-diazabicyclo[5.4.0]undec-7-ene
DIBAL=diisobutylaluminum hydride
DMAP=4-(dimethylamino)pyridine
DMF=N,N-dimethylformamide
$Et_3N$=triethylamine
GST glutathione transferase
LDA=lithium diisopropylamide
m-CPBA=metachloroperbenzoic acid
MMPP=monoperoxyphtalic acid
MPPM=monoperoxyphthalic acid, magnesium salt $6H_2O$
MS=methanesulfonyl=mesyl=$SO_2Me$
MsO=methanesulfonate=mesylate
NSAID=non-steroidal anti-inflammatory drug
OXONE®=$2KHSO_5 \cdot KHSO_4 \cdot K_2SO_4$
PCC=pyridinium chlorochromate
PDC=pyridinium dichromate
PDE phosphodiesterase
Ph=phenyl
Phe=benzenediyl
Pye=pyridinediyl
r.t.=room temperature
rac.=racemic
SAM=aminosulfonyl or sulfonamide or $SO_2NH_2$
SPA scientillation proximity assay
TBAF=tetra-n-butylammonium fluoride
Th=2- or 3-thienyl
TFAA=trifluoroacetic acid anhydride
THF=tetrahydrofuran
Thi=thiophenediyl
TLC=thin layer chromatography
TMS-CN=trimethylsilyl cyanide
Tz=1H (or 2H)-tetrazol-5-yl
$C_3H_5$=allyl
Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl

EXAMPLE 1

(R)-4-{2-(3-Cyclopentyloxy-4-methoxyphenyl)-2-[4-(4-methylpiperazinocarbonyl)phenyl]ethyl}pyridine A solution of carboxylic acid 2 (100 mg, 0.24 mmol), 1-methylpiperazine (0.03 mL, 0.26 mmol), diethyl cyanophosphonate (0.05 mL, 0.31 mmol) and triethylamine (0.05 mL, 0.34 mmol) in DMF (2 mL) was stirred at room temperature for 16 hours before EtOAc was added. The organic phase was washed with water and brine, dried ($MgSO_4$) and evaporated. The residue was purified by flash-chromatography (silica gel, $CH_2Cl_2$/MeOH 90:10) to afford the title compound as a white solid (60 mg, 50%). $^1$H NMR (400 MHz, $CDCl_3$): d 1.55 (m, 2H), 1.75 (m, 6H), 2.30 (s, 3H), 2.30 (m, 2H), 2.45 (m, 2H), 3.30 (d, 2H), 3.40 (m, 2H), 3.75 (m, 2H), 3.80 (s, 3H), 4.15 (t, 1H), 4.60 (m, 1H), 6.60 (s, 1H), 6.65 (d, 1H), 6.75 (d, 1H), 6.90 (d, 2H), 7.20 (d, 2H), 7.30 (d, 2H), 8.40 (d, 2H).

EXAMPLE 2

(R)-4-[2-(3-Cyclopentyloxy-4-methoxyphenyl)-2-(4-pyrrolidinocarbonylphenyl)ethyl]pyridine Following the procedure described in Example 1 but substituting pyrrolidine for 1-methylpiperazine, the title product was obtained as an off-white solid. $^1$H NMR (400 MHz, CDCl$_3$): d 1.55 (m, 2H), 1.80 (m, 8H), 1.95 (m, 2H), 3.30 (d, 2H), 3.40 (t, 2H), 3.60 (t, 2H), 3.80 (s, 3H), 4.15 (t, 1H), 4.60 (m, 1H), 6.60 (s, 1H), 6.65 (d, 1H), 6.75 (d, 1H), 6.90 (d, 2H), 7.20 (d, 2H), 7.45 (d, 2H), 8.40 (d, 2H).

EXAMPLE 3

(R)-4-[1-(3-Cyclopentyloxy-4-methoxyphenyl)-2-(4-pyridyl) ethyl]benzaldehyde oxime Hydroxylamine hydrochloride (100 mg, 1.4 mmol) was added to a solution of aldehyde 1 (406 mg, 1.0 mmol) in pyridine (4 mL) and the reaction mixture was stirred at room temperature for 18 hours. The volatiles were then evaporated and EtOAc was added to the residue. The organic phase was washed with 5% aqueous NaHCO$_3$, dried (MgSO$_4$) and evaporated. The residue was purified by flash-chromatography (silica gel, CH$_2$Cl$_2$/MeOH 95:5) to afford the title compound as a white solid (306 mg, 89%). $^1$H NMR (400 MHz, CDCl$_3$): d 1.55 (m, 2H), 1.80 (m, 6H), 3.30 (d, 2H), 3.80 (s, 3H), 4.15 (t, 1H), 4.65 (m, 1H), 6.60 (s, 1H), 6.65 (d, 1H), 6.75 (d, 1H), 6.90 (d, 2H), 7.20 (d, 2H), 7.45 (d, 2H), 7.60 (s, 1H), 8.10 (s, 1H), 8.40 (d, 2H).

EXAMPLE 4

(R)-4-{2-(3-Cyclopentyloxy-4-methoxyphenyl)-2-[4-(tetrazol-5-yl)phenyl]ethyl}pyridine Step 1:
(R)-4-[1-(3-Cyclopentyloxy-4-methoxyphenyl)-2-(4-pyridyl)ethyl]benzenenitrile Trichloromethyl chloroformate (0.18 mL, 1.5 mmol) was added to a 0° C. solution of (R)-4-[1-(3-cyclopentyloxy-4-methoxyphenyl)-2-(4-pyridyl)ethyl]benzaldehyde oxime from Example 3 (425 mg, 1.0 mmol) in acetonitrile (4 mL). The reaction mixture was stirred at room temperature for 1 hour before water was added. The mixture was then extracted with EtOAc. The organic phase was washed with 5% aqueous NaHCO$_3$, water and brine, dried (MgSO$_4$) and evaporated to afford the title compound as an off-white solid (350 mg, 86%).

Step 2:
(R)-4-{2-(3-Cyclopentyloxy-4-methoxyphenyl)-2-[4-(tetrazol-5-yl)phenyl]ethyl}pyridine A solution of (R)-4-[1-(3-cyclopentyloxy-4-methoxyphenyl)-2-(4-pyridyl)ethyl]benzene-nitrile from Step 1 (350 mg, 0.88 mmol) and tributyltin azide (1.17 g, 3.5 mmol) in 1,2-dichlorobenzene (4 mL) was stirred at 150° C. for 2 hours. The reaction mixture was then cooled to room temperature and acetic acid (0.5 mL) was added. After 15 min, aqueous 1N NaOH was added and the aqueous phase was washed 3 times with ether. The aqueous phase was then treated with 25% aqueous NH$_4$OAc and 6N HCl to pH 7 before it was extracted twice with CH$_2$Cl$_2$. The organic phase was then dried (MgSO$_4$) and evaporated to afford the title compound as a yellow solid (341 mg, 88%). $^1$H NMR (400 MHz, CDCl$_3$): d 1.55 (m, 2H), 1.80 (m, 6H), 3.30 (m, 1H), 3.45 (m, 1H), 3.80 (s, 3H), 4.20 (m, 1H), 4.70 (m, 1H), 6.70 (s, 1H), 6.80 (m, 2H), 7.00 (d, 2H), 7.20 (d, 2H), 7.90 (d, 2H), 8.40 (d, 2H).

EXAMPLE 5

(R)-4-{2-(3-Cyclopentyloxy-4-methoxyphenyl)-2- [4-(1-hydroxyethyl) phenyl]ethyl}pyridine Methylmagnesium bromide (1.4M solution in toluene-THF; 1.1 mL, 1.5 mmol) was added dropwise to a −78° C. solution of aldehyde 1 (509 mg, 1.3 mmol) in THF (4 mL) and the mixture was allowed to warm to room temperature. After 6 hours, 5% aqueous NaHCO$_3$ was added and the mixture was extracted twice with EtOAc. The organic phase was washed with brine, dried (MgSO$_4$) and evaporated. The residue was purified by flash-chromatography silica gel, hexane/EtOAc 25:75) to afford the title compound as a colorless gum (275 mg, 52%). $^1$H NMR (400 MHz, CDCl$_3$): d 1.45 (d, 3H), 1.55 (m, 2H), 1.75 (m, 6H), 2.40 (s, 1H), 3.30 (m, 2H), 3.80 (s, 3H), 4.15 (t, 1H), 4.65 (m, 1H), 4.85 (m, 1H), 6.60 (s, 1H), 6.65 (d, 1H), 6.70 (d, 1H), 6.90 (d, 2H), 7.15 (d, 2H), 7.25 (d, 2H), 8.30 (d, 2H).

EXAMPLE 6

(R)-4-[2-(3-Cyclopentyloxy-4-methoxyphenyl)-2-(4-acetylphenyl) ethyl]pyridine

A solution of (R)-4-{2-(3-cyclopentyloxy-4-methoxyphenyl)-2-[4-(1-hydroxyethyl)-phenyl]ethyl}pyridine from Example 5 (205 mg, 0.49 mmol) in CH$_2$Cl$_2$ (4 mL) was added to a suspension of pyridinium chlorochromate (272 mg, 1.3 mmol) and molecular sieve in CH$_2$Cl$_2$ (3 mL). The reaction mixture was stirred at room temperature for 1 hour before the volatiles were evaporated. The residue was then triturated in EtOAc and filtered over celite. Evaporation of the filtrate afforded a residue which was purified by flash-chromatography (silica gel, hexane/EtOAc 25:75) to afford the title compound as a white foam (39 mg, 19%). $^1$H NMR (400 MHz, CDCl$_3$): d 1.55 (m, 2H), 175 (m, 6H), 2.55 (s, 3H), 3.30 (d, 2H), 3.80 (s, 3H), 4.20 (t, 1H), 4.65 (m, 1H), 6.60 (s, 1H), 6.65 (d, 1H), 6.75 (d, 1H), 6.90 (d, 2H), 7.25 (d, 2H), 7.85 (d, 2H), 8.40 (d, 2H).

PREPARATION OF INTERMEDIATES

INTERMEDIATE 1:
(R)-4-[1-(3-Cyclopentyloxy-4-methoxyphenyl)-2-(4-pyridyl) ethyl]benzaldehyde.

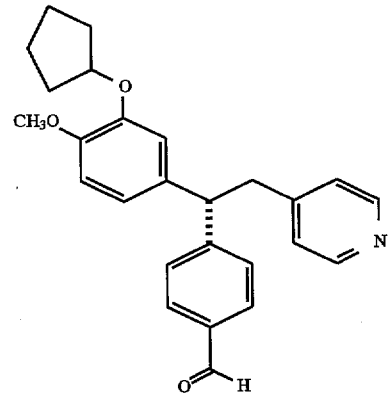

Step 1: 2-(4-Bromophenyl)-1,3-dioxolane

A solution of 4-bromobenzaldehyde (66.5 g, 359 mmol), ethylene glycol (22 mL, 395 mmol) and p-toluenesulfonic acid monohydrate (120 mg) in benzene (400 mL) was refluxed for 3 hours with concomitant Dean-Stark water trapping. The organic phase was then washed successively with 5% aqueous NaHCO$_3$, water and brine, dried (MgSO$_4$) and evaporated. The residue was distilled under reduced pressure (bp: 112° C./0.4 mm Hg) to afford the title compound as a colorless liquid (79.8 g, 97%).

Step 2: (1R, 5S)-N-{(3R)-3-(3-Cyclopentyloxy-4-methoxyphenyl)-3-[4-(1,3-dioxolan-2-yl)phenyl]-2-(4-pyridyl)propanoyl}-10,10-dimethyl-3-thia-4-azatricyclo [5.2.1.0$^{1.5}$]decane-3,3-dioxide A solution of 2-(4-bromophenyl)-1,3-dioxolane from Step 1 (55.3 g, 241 mmol) in THF (40 mL) was added to magnesium turnings (6.16 g, 254 mmol) in THF (140 mL) containing 1,2-dibromoethane (0.1 mL) at a sufficient rate to maintain a gentle reflux. The mixture was stirred at room temperature for 2 hours before the solution was added dropwise to a 0° C. solution of acyl sultam II (Celltech, World Patent Application 95/17386, 29 Jun. 1995) (43.2 g, 80.5 mmol) in THF (700 mL). The reaction mixture was stirred at room temperature for 16 hours before 10% aqueous $NH_4Cl$ was added. The mixture was extracted with EtOAc and the organic phase was washed with water and brine, dried ($MgSO_4$) and evaporated. The residue was recrystallized twice in EtOH to afford the title compound as an off-white solid (25.6 g, 46%).

Step 3:(R)-4-[1-(3-Cyclopentyloxy-4-methoxyphenyl)-2-(4-pyridyl)ethyl]benzaldehyde n-Butyllithium (2.4M solution in hexane; 10.6 mL, 25 mmol) was added dropwise to a 0° C. solution of propanethiol (4.6 mL, 51 mmol) in THF (150 mL). After 15 minutes, (1R, 5S)-N-{(3R)-3-(3-Cyclopentyloxy-4-methoxyphenyl)-3-[4-(1,3-dioxolan-2-yl)phenyl]-2-(4-pyridyl)propanoyl}-10,10-dimethyl-3-thia-4-azatricyclo[5.2.1.0$^{1,5}$]decane-3,3-dioxide from Step 2 (9.7 g, 14.1 mmol) was added as a solid and the reaction mixture was stirred at room temperature for 3 days. The volatiles were then evaporated and the resulting residue was dissolved in EtOH (80 mL) and water (40 mL). Sodium hydroxide (4.5 g, 113 mmol) was added and the mixture heated to reflux for 2 hours. The reaction mixture was cooled to room temperature and treated with HCl 6N to pH 4.5 then heated to reflux for 1 hour. The reaction mixture was cooled to room temperature and treated with NaOH 1N to pH 14 then extracted twice with EtOAc. The organic phase was washed with brine, dried ($MgSO_4$) and evaporated. The residue was purified by flash-chromatography (silica gel, ether) to afford the tire compound as a white foam (2.3 g, 41%). $^1$H NMR (400 MHz, $CDCl_3$): d 1.55 (m, 2H), 1.75 (m, 6H), 3.30 (m, 2H), 3.80 (s, 3H), 4.20 (t, 1H), 4.60 (m, 1H), 6.60 (s, 1H), 6.65 (d, 1H), 6.75 (d, 1H), 6.90 (d, 2H), 7.35 (d, 2H), 7.75 (d, 2H), 8.40 (d, 2H), 9.95 (s, 1H).

Intermediate 2:
(R)-4-[1-(3-Cyclopentyloxy-4-methoxyphenyl)-2-(4-pyridyl)ethyl]benzoic acid

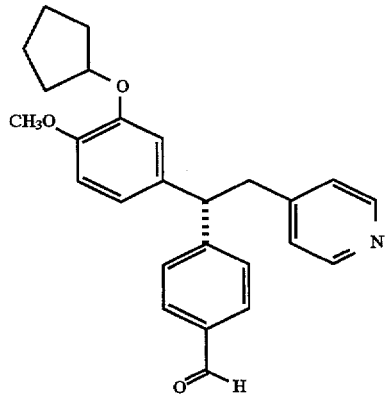

A solution of $NaClO_2$ (149 mg, 1.64 mmol) and $NaH_2PO_4 \cdot H_2O$ (227 mg, 1.64 mmol) in water (1 mL) was added to a solution of aldehyde 1 (508 mg, 1.27 mmol) and 2-methyl-2-butene (0.94 mL, 8.9 mmol) in t-BuOH (6 mL). The reaction mixture was stirred at room temperature for 19 hours before 25% aqueous $NH_4OAc$ was added. The mixture was then extracted twice with EtOAc. The organic phase was washed with brine, dried ($MgSO_4$) and evaporated to afford the title compound as a white solid (540 mg). $^1$H NMR (400 MHz, $CDCl_3$): d 1.55 (m, 2H), 1.75 (m, 6H), 3.35 (m, 2H), 3.80 (s, 3H), 4.20 (t, 1H), 4.60 (m, 1H), 6.60 (s, 1H), 6.65 (d, 1H), 6.75 (d, 1H), 7.00 (d, 2H), 7.25 (d, 2H), 8.00 (d, 2H), 8.45 (d, 2H).

What is claimed is:

1. A compound of formula I

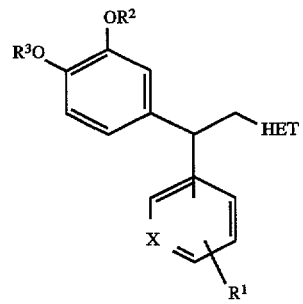

or a pharmaceutically acceptable salt thereof wherein:
$R^1$ is selected from (a) —CH=NOH, (b) 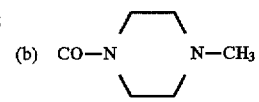

(c) 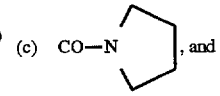, and (d) —5—tetrazolyl;

$R^2$ and $R^3$ are independently selected from (a) $C_{1-7}$alkyl wherein said alkyl is selected from a linear, branched and cyclic alkyl, (b) substituted $C_{1-7}$ alkyl, wherein the substituent is F, Cl, Br or I, (c) 2-phenethyl or 2-indanyl, optionally mono or di-substituted on the benzene ring, wherein the substituents are independently selected from the group consisting of (1) halo, (2) $C_{1-6}$alkoxy, (3) $C_{1-6}$alkylthio, (4) CN, (5) $CF_3$, (6) $C_{1-6}$alkyl, (7) $N_3$, (8) —$CO_2H$, $R^4$ is selected from (a) hydrogen, (b) $C_{1-6}$alkyl, (c) phenyl, benzyl or 2-phenethyl, optionally mono or di-substituted on the benzene ring, wherein the substituents are independently selected from the group consisting of (1) halo, (2) $C_{1-6}$alkoxy, (3) $C_{1-6}$alkylthio, (4) CN, (5) $CF_3$, (6) $C_{1-6}$alkyl,
(7) $N_3$,
(8) —$CO_2H$, $R^5$ and $R^8$ are each independently selected from
(a) —$CF_3$,
(b) $C_{1-6}$alkyl,
(c) phenyl, benzyl or 2-phenethyl, optionally mono or di-substituted on the benzene ring, wherein the substituents are independently selected from the group consisting of
(1) halo,
(2) $C_{1-6}$alkoxy,
(3) $C_{1-6}$alkylthio,
(4) CN,
(5) $CF_3$,
(6) $C_{1-6}$alkyl,
(7) $N_3$,
(8) —$CO_2H$, $R^6$ and $R^7$ are independently selected from
(a) hydrogen, and
(b) $C_{1-6}$alkyl, or $R^6$ and $R^7$ may be joined to form a saturated 5, 6 or 7 membered heterocycle, said heterocycle containing a heteroatom which is nitrogen and optionally containing an additional hetero atom which is O or S atom or $NR^4$, and optionally containing a carbonyl group;

HET is selected from
pyridyl or imidazolyl, optionally mono or di-substituted with substituents selected from the group consisting of halo, $C_{1-6}$alkyl, $C_{1-6}$alkoxy, $C_{1-6}$alkylthio, benzyl, 2-phenethyl, $NHCOR^5$, $NR^6R^7$, $NHS(O)_2R^8$, OH, CN, or $CF_3$, and the N-oxides thereof;

X is selected from N, N→O or CH.

2. A compound according to claim 1 wherein
$R^2$ is cyclopentyl, optionally mono or di or tri-substituted with substituents selected from the group consisting of F, Cl, Br and I, and
$R^3$ is methyl.

3. A compound according to claim 1 wherein
$R^1$ is selected from
(a) —CH=NOH,
(b) —CO—$N[CH_2CH_2]_2N$—$CH_3$;
(c) —CO—$N[CH_2CH_2CH_2CH_2]$, and
(d) —5—tetrazolyl;
$R^2$ is cyclopentyl,
$R^3$ is methyl,
$R^5$ and $R^8$ are each independently selected from
(a) —$CF_3$,
(b) $C_{1-3}$alkyl,
(c) phenyl, benzyl or 2-phenethyl, optionally mono or di-substituted on the benzene ring, wherein the substituents are independently selected from the group consisting of
(1) halo,
(2) $C_{1-3}$alkoxy,
(3) $C_{1-3}$alkylthio,
(4) CN,
(5) $CF_3$,
(6) $C_{1-3}$alkyl,
(7) $N_3$,
(8) —$CO_2H$, $R^6$ and $R^7$ are independently selected from
(a) hydrogen, and
(b) $C_{1-3}$alkyl, or $R^6$ and $R^7$ may be joined to form a saturated 5, 6 or 7 membered heterocycle, said heterocycle containing a heteroatom which is nitrogen and optionally containing an additional hetero atom which is O or S atom or $NR^4$, and optionally containing a carbonyl group;

HET is selected from
pyridyl or imidazolyl, optionally mono or di-substituted with substitutents selected from the group consisting of halo, $C_{1-6}$alkyl, $C_{1-6}$alkoxy, $C_{1-6}$alkylthio, benzy, 2-phenethyl, $NHCOR^5$, $NR^6R^7$, $NHS(O)_2R^8$, OH, CN, or $CF_3$, and the N-oxides thereof;

X is selected from N, N→O or CH.

4. A compound according to claim 3 wherein $R^1$ is selected from
(a) —CH=NOH,
(b) —CO—$N[CH_2CH_2]_2N$—$CH_3$;
(c) —CO—$N[CH_2CH_2CH_2CH_2]$, and
(d) —5—tetrazolyl;
$R^2$ is cyclopentyl,
$R^3$ is methyl,
$R^5$ and $R^8$ are each independently selected from
(a) —$CF_3$,
(b) $C_{1-3}$alkyl,
$R^6$ and $R^7$ are independently selected from
(a) hydrogen, and
(b) $C_{1-3}$alkyl, or
$R^6$ and $R^7$ may be joined to form a saturated 5, 6 or 7 membered heterocycle, said heterocycle containing a heteroatom which is nitrogen and optionally containing an additional hetero atom which is O or S atom or $NR^4$, and optionally containing a carbonyl group;

HET is selected from
pyridyl, optionally mono or di-substituted with substitutents selected from the group consisting of halo, $C_{1-6}$alkyl, $C_{1-6}$alkoxy, $C_{1-6}$alkylthio, benzyl, 2-phenethyl, $NHCOR^5$, $NR^6R^7$, $NHS(O)_2R^8$, OH, CN, or $CF_3$, and the N-oxides thereof;

X is CH.

5. A compound according to claim 1 selected from the group consisting of
(a) (R)-4-{2-(3-Cyclopentyloxy-4-methoxyphenyl)-2-[4-(4-methylpiperazinocarbonyl)phenyl]ethyl}pyridine,
(b) (R)-4-[2-(3-Cyclopentyloxy-4-methoxyphenyl)-2-(4-pyrrolidinocarbonylphenyl)ethyl]pyridine,
(c) (R)-4-[1-(3-Cyclopentyloxy-4-methoxyphenyl)-2-(4-pyridyl)ethyl]benzaldehyde oxime,
(d) (R)-4-{2-(3-Cyclopentyloxy-4-methoxyphenyl)-2-[4-(tetrazol-5-yl)phenyl]ethyl}pyridine,
(e) (R)-4-{2-(3-Cyclopentyloxy-4-methoxyphenyl)-2-[4-(1-hydroxyethyl) phenyl]ethyl}pyridine, and
(f) (R)-4-[2-(3-Cyclopentyloxy-4-methoxyphenyl)-2-(4-acetylphenyl) ethyl]pyridine,
or a pharmaceutically acceptable salt thereof.

6. A pharmaceutical composition for treating asthma comprising:
a non-toxic therapeutically effective amount of a compound according to claim 1 and a pharmaceutically acceptable carrier.

7. A pharmaceutical composition for treating disease by increasing the cellular level of cAMP, comprising:

a non-toxic therapeutically effective amount of a compound according to claim 1 and a pharmaceutically acceptable carrier.

8. A method of treating asthma comprising:

administration to a patient in need of such treatment of a non-toxic therapeutically effective amount of a compound according to claim 1 and a pharmaceutically acceptable carrier.

9. A method of treating disease by inhiting PDE IV comprising:

administration to a patient in need of such treatment of a non-toxic therapeutically effective amount of a compound according to claim 1.

* * * * *